United States Patent [19]
Synodis et al.

[11] Patent Number: 6,034,138
[45] Date of Patent: Mar. 7, 2000

[54] DISINFECTANT COMPOSITION

[75] Inventors: Joseph Synodis, Summit; Stuart Wilensky, Matawan; Alan Halecky, West Orange, all of N.J.

[73] Assignee: Block Drug Company, Inc., Jersey City, N.J.

[21] Appl. No.: 08/561,578

[22] Filed: Nov. 21, 1995

[51] Int. Cl.[7] .......................... A01N 31/02; A01N 33/24; A01N 35/00; A01N 41/00

[52] U.S. Cl. .......................... 514/640; 514/557; 514/568; 514/705; 514/711; 514/724; 424/613; 424/662; 424/657; 424/660; 424/667; 424/668; 424/703; 424/709; 424/715; 422/36

[58] Field of Search ................................ 514/557, 568, 514/640, 705, 711, 724; 422/36; 424/613, 662, 657, 660, 667, 668, 703, 709, 715

[56] References Cited

U.S. PATENT DOCUMENTS

| | | | |
|---|---|---|---|
| 3,983,252 | 9/1976 | Buchalter | 514/698 |
| 4,523,038 | 6/1985 | Scott et al. | 568/492 |
| 5,284,621 | 2/1994 | Kaufman | 422/32 |
| 5,322,856 | 6/1994 | Martin | 514/574 |
| 5,411,990 | 5/1995 | Tsuji et al. | 514/640 |
| 5,480,643 | 1/1996 | Donovan et al. | 424/409 |

*Primary Examiner*—John Pak

[57] ABSTRACT

The present invention comprises a concentrated solid or semi-solid disinfectant or sterilant composition for use in an aqueous disinfecting or sterilizing solution, comprising an oxidant and a protected glutaraldehyde such as a glutaraldehyde bisulfite addition compound (GBS):

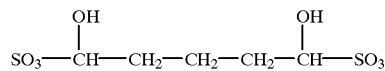

or a glutaraldehyde dioxime compound (GDO):

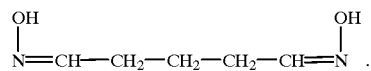

The present invention further provides a method for disinfecting or sterilizing a surface or apparatus comprising the steps of mixing a concentrated solid or semi-solid glutaraldehyde sterilant composition comprising an oxidizing compound and a protected sterilant with water to form a solution and bringing the solution into contact with the surface or apparatus.

7 Claims, No Drawings

DISINFECTANT COMPOSITION

FIELD OF THE INVENTION

The invention relates to concentrated sterilant compositions and sterilant solutions made from the concentrated sterilant compositions and to methods for making and using such sterilant compositions.

BACKGROUND OF THE INVENTION

Heat sterilization is the preferred method to disinfect or sterilize items and surfaces that need to be germ-free during use, such as surgical and dental instruments and environmental surfaces utilized in these environments. Unfortunately, heat treatment is not acceptable for some materials, like rubber gloves, thermometers and other heat-degradable or heat-sensitive instruments and surfaces that are usually found in medical and dental environments. Heat is also not usually appropriate for surface areas of tables, chairs, sinks and the like which actually comprise the environment which must be kept substantially germ-free. These must be treated using chemical disinfectants and sterilants.

Sterilant solutions have been used for many years to disinfect and sterilize medical instruments, dental instruments and other articles, tools, and surfaces that must be germ-free during operation or use. Sterilant solutions may also be used to disinfect and treat medical and other wastes that may pose a environmental hazard if not disposed of properly. These solutions are primarily aqueous in nature and comprise a low concentration of a highly potent germicide.

In the past, sterilant solutions have been purchased in dilute liquid form and applied directly to the surface to be treated. These dilute aqueous solutions are heavy, difficult to store, cumbersome and are subject to spillage and degradation. Concentrating these aqueous solutions is not an adequate remedy as it still results in difficult bulk transportation and safety problems.

Concentrated sterilants, in the form of solids or semi-solids, would avoid the difficulties and safety concerns inherent in storing and moving large volumes of dilute aqueous sterilant solutions. This highly concentrated form of the sterilant takes up far less space, is less bulky and there is a lesser probability of spillage and loss. The difficulty with some concentrated systems however, is that many sterilants in this state will not readily dissolve to form an aqueous solution.

Types of known sterilant solutions are dilute aqueous solutions of a strong effective crosslinking agent, one class being the dialdehydes. One common dialdehyde that is particularly effective in this fashion is glutaraldehyde whose chemical structure is as follows:

O=CH—CH$_2$—CH$_2$—CH$_2$—CH=O

Conventional glutaraldehyde sterilant systems usually comprise only about 2.0% by weight of glutaraldehyde. Additionally, these systems often contain a non-ionic surfactant, a chelating agent, and a buffer. An object to be sterilized is simply immersed into the solution as with surgical and dental instruments, or the solution is applied by any one of a number of means to a surface to be sterilized such as surgical platforms or dental side tables.

One glutaraldehyde sterilant system is set forth in U.S. Pat. No. 5,284,621 to Kaufman, issued Feb. 8, 1994. That patent discloses treatment of medical waste fluids using a xerogel comprised of at least one water insoluble hydrophilic polymer and glutaraldehyde. The xerogel absorbs aqueous ingredients in waste fluids, and the glutaraldehyde disinfects the fluids. The patent discloses that the glutaraldehyde may be formulated as a bisulfite addition product in a solid form such as free-flowing powders so as to prevent reaction with the xerogel prior to use, yet would decompose upon exposure to the mildly acidic or alkaline conditions of the waste fluids. Unfortunately, aldehydes (i.e. glutaraldehyde) are fairly reactive and have a tendency to react with the xerogels disclosed and claimed in this patent. To avoid reaction of the glutaraldehyde with the xerogels, the disclosure teaches that such problems might be precluded by using solid derivatives of the disinfectants which would not be reactive with the xerogels. These derivatives could then be effectively distributed throughout the xerogel and could easily decompose and be released upon contact with the waste fluids to yield the desired disinfectant. Suggested suitable derivatives include the bisulfite addition products of carbonyl group-containing compounds such as glutaraldehyde which are easily decomposed to form the carbonyl group containing composition and the bisulfite under the mildly acidic or alkaline conditions usually found in the collected fluids.

Another patent, U.S. Pat. No. 3,983,252 to Buchalter, issued Sep. 28, 1976 is directed to disinfectant compositions that contain a dialdehyde and the alkali metal salt of a hydrocarbon carboxylic acid in aqueous solution and, optionally, an alcohol and/or a diol and/or a triol. The dialdehyde may be in its pure form, its acid form or in the form of an adduct such as an alkali metal bisulfite adduct, glutaraldehyde bisulfite. The disinfectant may also comprise a nitrogenous adduct such as glutaraldehyde dioxime. Although the main goal of the patent is the long term stability of aqueous glutaraldehyde formulations, the dialdehyde component may also be formulated as a solid.

Glutaraldehyde has also been used for purposes other than disinfection such as functioning as a stabilizer in color photographic film.

Despite the known use of glutaraldehyde as a sterilant and/or disinfectant, and despite the known use of solid glutaraldehyde derivatives in treating waste fluids, there is a strong need in the art for a concentrated, solid or semi-solid sterilant composition with several important properties never before provided by the prior art. In order for a solid or semi-solid sterilant to be of any value, the composition must be sufficiently stable to avoid decomposition during long term storage and it must be substantially impervious to the presence of moisture. On the other hand however, the composition must also be sufficiently reactive when mixed in solution to generate an effective dose of glutaraldehyde in a timely fashion as needed. The compositions must also be relatively safe to handle. And, preferably, the composition should be commercially available, or at least easily and reliably synthesized from commercially available materials.

Most importantly, however, the source of glutaraldehyde must be readily solubilized and activated as a sterilant solution with the reactive aldehyde groups not degraded or complexed with other ions during this solubilizing and mixing process.

SUMMARY OF THE INVENTION

The present invention comprises a concentrated sterilant composition for use in an aqueous sterilizing solution, comprising an oxidant and a protected glutaraldehyde such as a glutaraldehyde bisulfite addition compound (GSB):

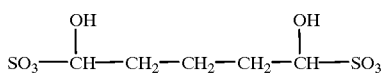

The present invention further provides a method for sterilizing or disinfecting a surface comprising the steps of mixing a concentrated glutaraldehyde sterilant composition comprising an oxidizing compound and a protected sterilant with water to form a solution and bringing the solution into contact with the surface.

DETAILED DESCRIPTION OF THE INVENTION.

The principal object of the present invention is to provide a semi-solid or solid glutaraldehyde-based sterilant composition. The major advantages of a solid or semi-solid form are its long term stability and the reduction in storage space required relative to conventional liquid-based sterilants.

Another object of the invention is to provide a glutaraldehyde solution that becomes active, i.e. bactericidal, fungicidal, tuberculocidal, virucidal and sporicidal, within minutes of forming the solution and remains effective for an extended period of time for up to several months. An advantage of the present invention is that it rapidly provides a strong glutaraldehyde sterilizing solution that is solubilized from a stable solid powder at a substantially neutral pH, thus allowing the solution to remain effective for an extended period of time for up to several months, but more typically about one month.

The invention comprises a solid or semi-solid composition that forms a sterilizing solution upon the addition of water. The solid or semi-solid composition comprises a protected sterilant, an alkaline salt to facilitate regeneration of the aldehyde, and a liberating oxidizing agent that reacts with the protective moiety when generated in solution to prevent regression of the aldehyde back to its derivative state. For purposes of the present application, a "solid or semi-solid" composition includes such forms as powders, traditional tablets, coated tablets, injection molded solids, soft or hard gelatin capsules, gels, ointments, creams and the like.

The sterilant useful in the practice of the present invention may actually be any known sterilization agent that is an effective germicide in an aqueous solution. Preferred agents are those compounds having at least one functional group capable of reversibly attaching a protecting ligand thereto. It is especially preferred that the compound resulting from attachment of the ligand be solid at temperatures and pressures ordinarily experienced during commercial packaging, storage and use. More preferred are disinfecting aldehyde compounds, and most preferred are the dialdehyde compounds. Of the dialdehydes, glutaraldehyde is the most preferred. Glutaraldehyde, however, is an oil at room temperature and is also subject to polymerization in water thereby posing difficulties for conversion to a solid or semi-solid system.

With respect to the protecting agents, any agent that reacts with the sterilant and produces a solid or semi-solid, generally nonreactive (in a dry environment) compound at room temperature and pressure is preferred. The ligand and the sterilant should readily dissociate in water thereby liberating the free form of the sterilant. Obviously, the by-products of the dissociation (i.e., the protecting ligand) must not interfere with the germicidal action of the sterilant. Neither should the products adhere to the surface being sterilized as a residue, nor should they stain, coat or discolor either the surface to be sterilized or the container used for the sterilization.

Preferred protecting agents are those that readily form covalent bonds with the selected sterilant. Such compounds are known as addition compounds. With glutaraldehyde, groups providing sulfite and oxime ligands to the aldehyde moieties are preferred, and sulfite ligands are especially preferred. Salts of these ligands, especially soluble alkali salts are most preferred due to the relative ease of solubilization.

The preferred addition compound of the invention is glutaraldehyde-bisulfite addition compound (GBS) or a glutaraldehyde dioxime (GDO).

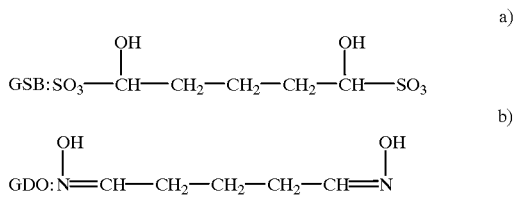

These compounds liberate glutaraldehyde through an equilibrium reaction, and not surprisingly, the amount of "free" glutaraldehyde increases with increasing pH. One advantage of using glutaraldehyde bisulfite or dioxime as a glutaraldehyde source is that the innocuous sulfite or ammonia that is released upon dissolution are the only byproducts of the decomposition of the glutaraldehyde addition compound. Other aldehyde derivatives upon decomposition might add undesirable contaminants to a sterilant solution. GBS and GDO are also stable in that they do not liberate glutaraldehyde upon mere standing during storage. They are also commercially available and are safer to handle than glutaraldehyde solution.

GBS is obtained by reacting sodium sulfite and glutaraldehyde in water at high pH (generally greater than 8.5) and then drying the resulting salt.

GDO is obtained by reacting hydroxylamine and glutaraldehyde in water, also at a high pH.

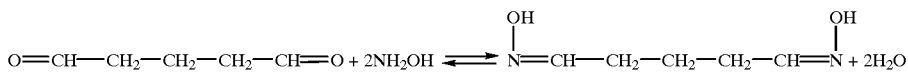

A 2.0% glutaraldehyde solution may be obtained from most solid or semi-solid compositions of glutaraldehyde bisulfite only at an unacceptably high pH due to the nature of the equilibrium reaction. As the pH is increased, the formation of glutaraldehyde is favored over the formation of glutaraldehyde bisulfite addition compound. However, above pH 8.5, the rate of glutaraldehyde polymerization becomes significant. Polymerization of glutaraldehyde diminishes its antimicrobial activity by decreasing the concentration of reactive aldehyde groups. Increasing the pH above 8.5 also shortens the effective lifetime of glutaraldehyde-based sterilant solutions.

The problem that arises then is that at the higher pH environments wherein glutaraldehyde formation from the bisulfite addition compound is favored, the polymerization and deactivation of glutaraldehyde is also favored. It was discovered that one way in which glutaraldehyde can be completely liberated from the bisulfite protective group once it is dissolved in solution at lower pH values is by shifting the equilibrium of the reaction toward glutaraldehyde formation while using a suitable buffer to hold the pH range from 8.0 to 8.5, the optimal operating range of most commercial glutaraldehyde based sterilants. This is accomplished by removing sulfite from the right side of the reaction equation by oxidizing it to sulfate. With the sulfite converted to sulfate, the reverse reaction of glutaraldehyde with sulfite is eliminated. The problem, of course, especially with glutaraldehyde, is to selectively oxidize the sulfite without also oxidizing the aldehyde groups of glutaraldehyde. Aldehyde groups are easily oxidized to carboxylate groups, which have no antimicrobial activity.

The equilibrium driving agent may be any compound that reacts with the dissociated sulfite or oxime protective ligand in preference to the aldehyde groups of the sterilant. It was discovered that preferred agents for oxidizing the protecting ligand include the alkali and alkaline earth metal salts of: percarbonates; persulfates; hypochlorites; superoxides; chlorites; peroxyacetates; hypobromites; hypoiodites; perborates; periodates; peroxides; peroxyformates; peroxybenzoates; chlorates; bromites; and chloroperoxybenzoates. More preferably, especially for GBS compounds, the oxidizing agents are sodium perborate and sodium percarbonate.

In addition to the glutaraldehyde derivative sterilant and the oxidizing agent, a buffering system may also be incorporated in the concentrated disinfection compound of the present invention in order to maintain the pH of the solution between 8.0–9.0 wherein glutaraldebyde sterilants are most potent. Suitable buffering agents include, but are not limited to sodium carbonate, potassium carbonate, their bicarbonate moieties and mixtures thereof. The amount of buffering agent incorporated in the disinfectant composition will depend on the amount of dry glutaraldehyde sterilant and oxidation agent which, again, is governed by the size of the application to be disinfected.

The invention further comprises a pouch containing a mixture of the concentrated ingredients and a kit containing the concentrated ingredients. Generally, a disinfectant solution may be prepared by dissolving the sterilant into a quart or gallon of water depending upon the size of the applica tion. A 2.0% solution will normally suffice to provide effective disinfectant and sterilant activity. This can then either be applied directly to the surfaces to be disinfected or sterilized using a sponge or cloth, or articles to be disinfected such as surgical instruments may be placed directly in said solution for an appropriate period of time. The preferred concentration of the formulation in solution is as follows:

| Ingredient | Concentration |
|---|---|
| Glutaraldehyde Bisulfite | 62.5 g/l |
| Sodium Perborate | 40.0 g/l |
| Sodium Carbonate | 5.0 g/l |

It will be apparent to those skilled in the art that various modifications and variations may be made in the apparatus or procedure of the invention. This could include the addition of surfactants, corrosion inhibitors, chelating agents, fragrances and dyes. To the extent that any such changes or modifications do not result in a negative material change or alter the characteristics of the final product, they are deemed as falling within the spirit and scope of the invention as recited by the claims that follow.

What we claim is:

1. A concentrated solid or semi-solid antimicrobial composition that forms a buffered sterilizing solution upon the addition of water for the disinfection and sterilization of contaminated surfaces, articles and fluids comprising:
   a) a protected glutaraldehyde sterilant;
   b) an oxidizing agent; and
   c) a buffer system.

2. The antimicrobial composition of claim 1 wherein said glutaraldehyde sterilant is protected by sulfite ligands, oxime ligands and mixtures thereof.

3. The antimicrobial composition of claim 2 wherein said sterilant is an alkali metal salt of a glutaraldehyde sterilant protected by sulfite ligands, oxime ligands and mixtures thereof.

4. The antimicrobial composition of claim 3 wherein said glutaraldehyde sterilant is selected from the group consisting of glutaraldehyde bisulfite, glutaraldehyde dioxime and mixtures thereof.

5. The antimicrobial composition of claim 4 wherein said oxidation agent is selected from the group consisting of alkali and alkaline earth metal salts of percarbonates, persulfates, hypoiodites, perborates, periodates, peroxides, peroxyformates, peroxybenzoates, chlorates, bromites, hypobromites and chloroperoxybenzoates and mixtures thereof.

6. The antimicrobial composition of claim 5 wherein said oxidation agent is selected from the group consisting of sodium perborate, sodium percarbonate and mixtures thereof.

7. The antimicrobial composition of claim 6 wherein said buffer is selected from the group consisting of sodium carbonate, potassium carbonate, potassium bicarbonate, sodium bicarbonate and mixtures thereof.

* * * * *